United States Patent [19]

Landgraf et al.

[11] Patent Number: 4,681,540
[45] Date of Patent: Jul. 21, 1987

[54] DENTAL HANDPIECE ARRANGEMENT

[75] Inventors: Hermann Landgraf; Werner Schuss, both of Heppenheim; Rainer-Karl Worschischek, Lorsch, all of Fed. Rep. of Germany

[73] Assignee: Siemens Aktiengesellschaft, Berlin and Munich, Fed. Rep. of Germany

[21] Appl. No.: 788,727

[22] Filed: Oct. 17, 1985

[30] Foreign Application Priority Data

Nov. 9, 1984 [DE] Fed. Rep. of Germany ....... 3441024

[51] Int. Cl.⁴ .............................................. A61C 1/08
[52] U.S. Cl. ..................................... 433/126; 433/29; 433/131
[58] Field of Search .................. 433/126, 131, 29; 310/58, 68 D

[56] References Cited

U.S. PATENT DOCUMENTS 3,604,960 9/1971 Krestel .
4,007,529 2/1977 Fleer .
4,184,256 1/1980 Loge et al. .
4,237,393 12/1980 Landgraf .
4,251,212 2/1981 Worschischek et al. .
4,271,596 7/1981 Weber et al. ...................... 433/131
4,460,337 7/1984 Landgraf et al. ...................... 433/29

FOREIGN PATENT DOCUMENTS 1048358 11/1966 United Kingdom .
1509605 7/1974 United Kingdom .

Primary Examiner—Robert Peshock
Attorney, Agent, or Firm—Hill, Van Santen, Steadman & Simpson

[57] ABSTRACT

An improved dental handpiece arrangement utilizes a drive cartridge containing the drive motor. The drive cartridge coacts with a coupling member and can be utilized with either a tubular adapter which enables use with one type of dental grip piece or can be utilized with a grip piece having an integral tubular portion for receiving the cartridge. The arrangement with the motor cartridge provides a great flexibility of utilizing grip pieces of different constructions.

19 Claims, 14 Drawing Figures

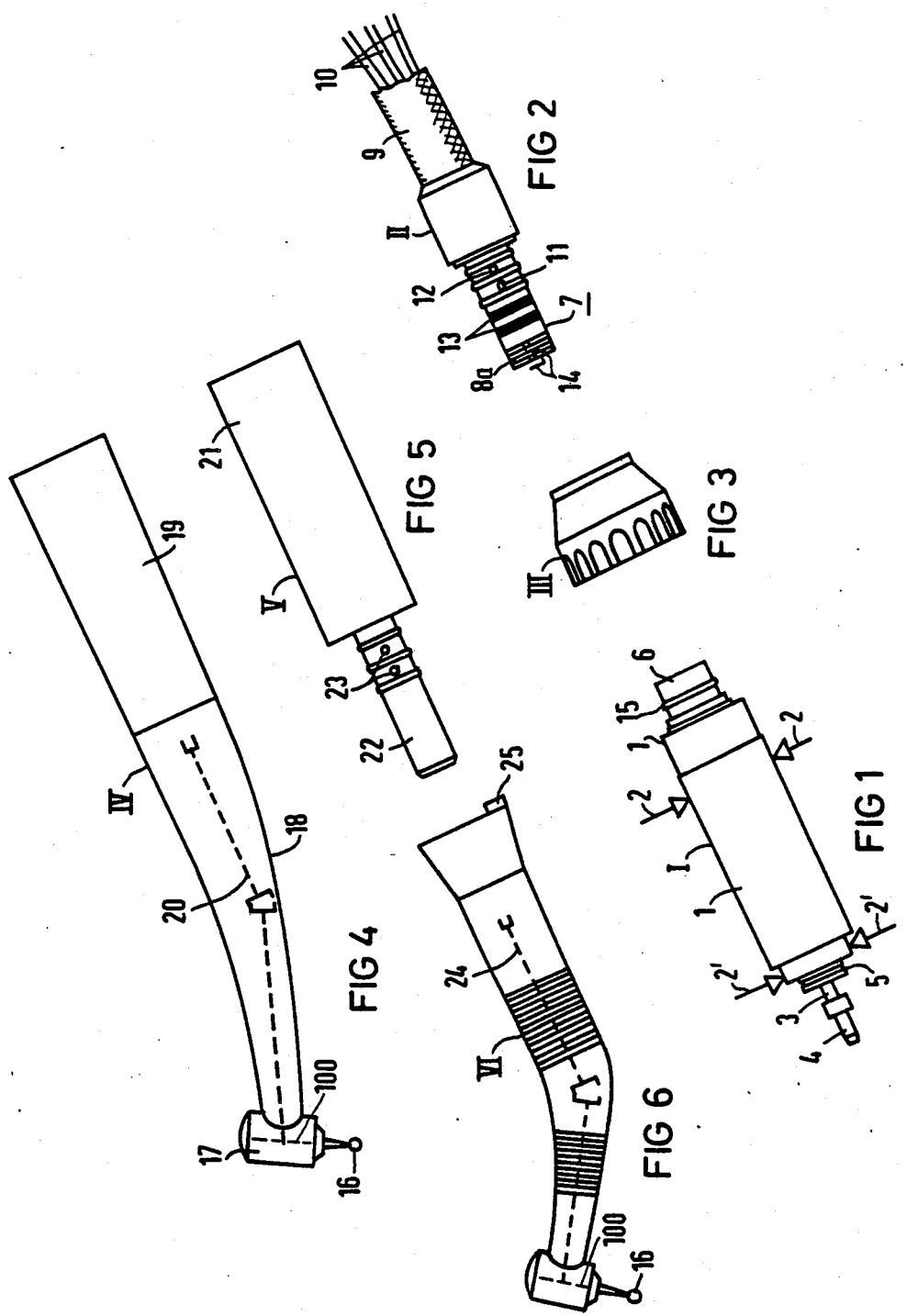

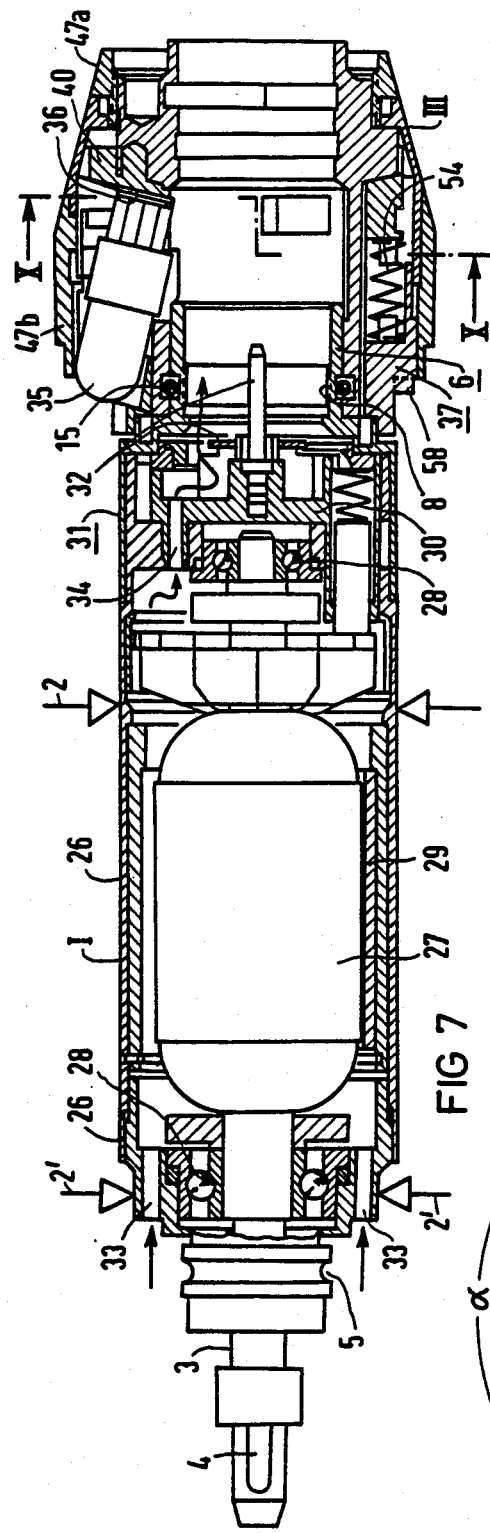

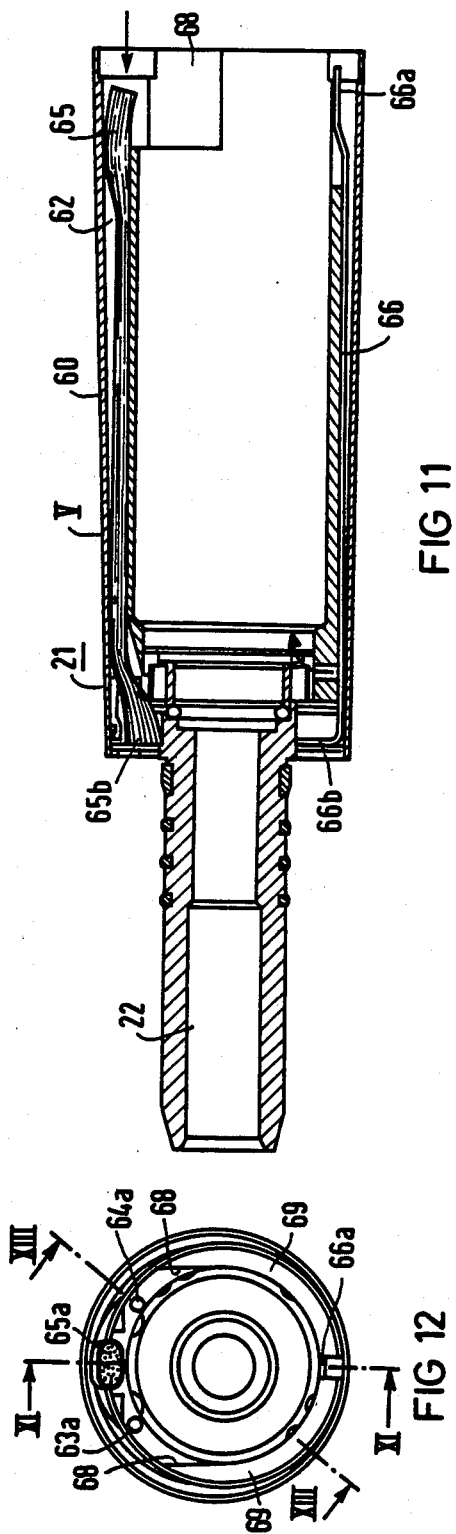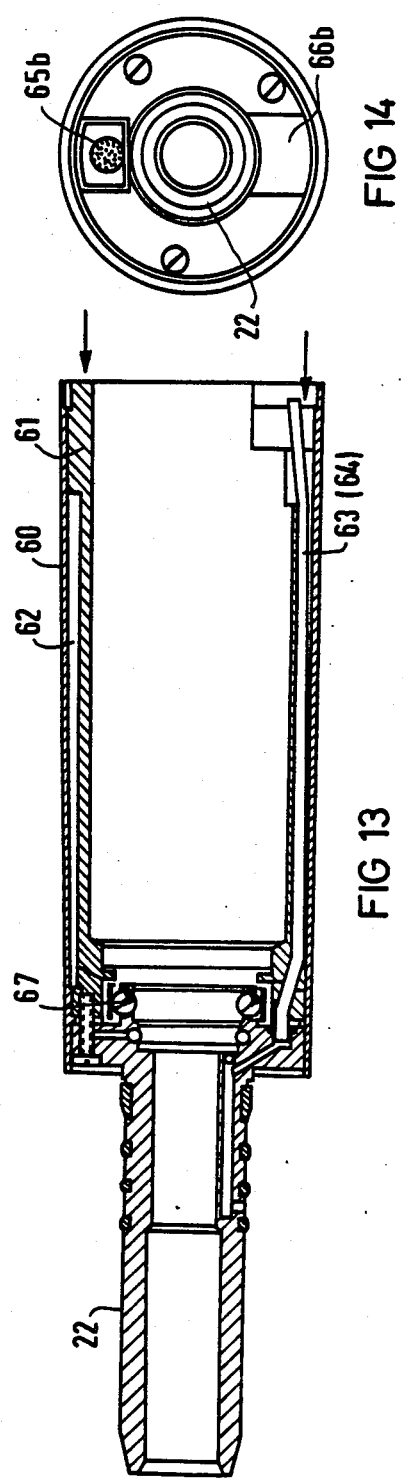

4,681,540

DENTAL HANDPIECE ARRANGEMENT

BACKGROUND OF THE INVENTION

The present invention is directed to a dental handpiece arrangement having a drive motor with a drive shaft and a grip piece containing a grip sleeve with a head housing having a chuck arrangement to hold a tool which is rotated by a drive train that is connected to the drive shaft of the drive motor.

It has been known for a long time in dental technology to mount with a removable connection a handpiece part essentially containing a head housing with a gripping sleeve connected thereto which is referred to in the technical field as a "hand and angle piece" on a drive part containing a drive motor. The connection is thereby designed such that in its emplaced condition, the hand and angle piece can be rotated relative to the drive part while retaining the drive shaft connection. The coupling and uncoupling occurs by means of a rapid coupling via a guide pin which surrounds the drive shaft of the drive part as disclosed in U.S. Pat. No. 3,604,960.

The construction of such a handpiece arrangement has been retained even with the introduction of what is referred to as an incorporated spray arrangement, i.e., the guidance of a cooling agent such as air and water within the drive parts and within the hand and angle piece. The guidance of the agent within the drive part is between the stator and motor housing and the agent is delivered at the guide pin for transfer to the grip piece through a fluid coupling arrangement which includes radially extending ports in one of the guide pins or socket of the grip piece and the other of the guide pins and socket having annular channels with O-ring seals for receiving the discharge from the ports. Such an arrangement is disclosed in U.S. Pat. No. 4,007,529.

In addition to these conventional handpiece arrangements, a handpiece arrangement wherein the gripping sleeve normally remains on the drive part and only relative short treatment heads containing the head housing are coupled to the drive part in an easily releasable fashion have also become common in recent years. The gripping sleeve will have a sleeve extending over the drive part which contains the agent guidance, and the gripping sleeve itself is only removed from the drive part for sterilization purposes. The gripping sleeve and the treatment head are freely rotatable relative to the drive part but the sleeve extending over the motor is not and it is capable of being withdrawn from the drive part together with the gripping sleeve as disclosed in U.S. Pat. No. 4,251,212.

In this handpiece system, the agent guidance occurs within the drive part and the agent delivery occurs via correspondingly fashioned fluid couplings between the guide pin and a socket in the handpiece.

Recently, it has become desirable to offer a motor-driven handpiece arrangement with an incorporated light guidance and this would initially mean providing additional variations of the handpieces with light guidance which handpieces would no longer be compatible with the handpiece arrangements heretofore commercially available. This would particularly affect the motor side where drives with and without light would have to be offered for coupling the one or the other handpiece systems explained above.

SUMMARY OF THE INVENTION

The present invention is directed to creating a handpiece arrangement with which a prerequisite is produced therefor, that one and the same drive motors can be provided both for the use of conventional hand and angle pieces as well as for the use of hand parts extending over the motor which are already known and under given conditions even other such handpiece parts whereby both light guiding handpieces as well as handpieces without light could be coupled to the drive motor.

These objects are accomplished by an improvement in a construction of a dental handpiece arrangement having a drive motor with a drive shaft, a grip piece having a head housing with chuck means to hold and rotate a tool, and a drive train extending in the grip piece to connect the drive shaft to the chuck means. The improvements comprise the drive motor being received in a cylindrical motor cartridge with the drive shaft extending out of a cylindrical coupling element at one end of the cartridge which coupling element has a smaller diameter than the diameter of the cartridge, said cartridge having a tubular heel of a smaller diameter than the major portion of the cartridge at the other end for releasable connection with a pin member of a supply hose containing electrical leads and water and air lines, said motor cartridge having at least two cylindrical bearing surfaces axially spaced therealong for coacting with internal bearing surfaces of a cylindrical sleeve which is telescopically received on the cartridge and may be a part of an adapter or a part of the grip piece, said cylindrical sleeve having a coupling element coacting with said cylindrical coupling elements to form latch means for securing the sleeve on the motor cartridge, and a sleeve-shaped coupling member being received on the tubular heel for rotation thereon, said sleeve-shaped coupling member having means forming fluid couplings for air and water discharging from the pin member and having means for transferring electrical energy from slip rings disposed on the surface of the pin member, said coupling member having fluid channels extending from the fluid coupling means to sockets for receiving fluid conduits of the sleeve member to form connections therewith so that fluid is coupled through the coupling member to the sleeve member and into passages of the grip piece to be discharged adjacent the chuck means, the coupling member and sleeve member having coacting parallel extending surfaces to form a plug-like connection between the sleeve member and coupling member as the sleeve member is telescopically received on the motor cartridge. The advantage of the improved device or handpiece is that the motor cartridge can receive the tubular member which is either a part of an adapter which will receive pre-existing grip pieces or can be a portion of a grip piece designed for use with the cartridge. Thus, the improvement provides a greater flexibility in the use of the device.

Since none of the light guides or cooling agent lines are conducted in the motor cartridge but rather are conducted through the coupling member into the tubular sleeve member, an adapter having the sleeve member can receive conventional hand and angle pieces which require the cooling and/or light lines. In addition, differently designed handpiece parts which are currently commercially available with or without light guidance means, can be used on a suitably constructed adapter. The heel portion, which has an outside diameter which is smaller in comparison than the outside diameter of the other parts on the motor cartridge, allows for the connection or, respectively, coupling lines for the agents to be provided in the coupling member. In addition, an incandescent lamp as a light source can be accommodated in a space-saving fashion in the coupling member for feeding light guiding elements in the tubular sleeve member.

Other advantages and developments will be readily apparent from the following description, drawings and claims.

BRIEF DESCRIPTION OF THE DRAWINGS

FIG. 1 is a side view of a motor cartridge of the present invention;

FIG. 2 is a side view of a connecting part for a supply hose in accordance with the present invention;

FIG. 3 is a side view of a coupling member in accordance with the present invention;

FIG. 4 is a side view of one type of handpiece having a gripping sleeve with a sleeve portion for receiving the motor cartridge in accordance with the present invention;

FIG. 5 is a side view of an adapter having a gripping sleeve portion for receiving the motor cartridge in accordance with the present invention;

FIG. 6 is a side view of an angled handpiece for use with the adapter of FIG. 5 in accordance with the present invention;

FIG. 7 is a longitudinal cross-sectional view with portions in elevation of the motor cartridge with the coupling member in accordance with the present invention;

FIG. 8 is a front end view of the motor cartridge and coupling member of FIG. 7;

FIG. 9 is a cross-sectional view taken along lines IX—IX of FIG. 8;

FIG. 10 is a cross-sectional view taken along lines X—X of FIG. 7;

FIG. 11 is a cross-sectional view of a tubular adapter of the present invention taken along lines XI—XI of FIG. 12;

FIG. 12 is an end view taken from the right end of the tubular adapter of FIG. 11;

FIG. 13 is a cross-sectional view taken along lines XIII—XIII of FIG. 12; and

FIG. 14 is an end view taken from the left end of the adapter of FIG. 11.

DESCRIPTION OF THE PREFERRED EMBODIMENTS

The principles of the present invention are particularly useful in a dental handpiece arrangement having a motor cartridge I of FIG. 1. The motor cartridge I comprises an essentially cylindrical element 1. which has two slide bearing surfaces indicated by the arrows 2 and 2' which are axially spaced along the axis of the cartridge and as illustrated, one of the slide bearing surfaces 2' is of a smaller diameter than the other bearing surface 2.

As best illustrated in FIG. 7, the motor cartridge I basically accepts only the motor parts such as the rotor 27 with a shaft 3, rotor shaft bearings 28, stator 29, brushes and brush mount 30. An end of the motor shaft 3 extends from one end of the cartridge I and is provided with a dog 4 which couples the shaft to corresponding drive sections of the handpiece part in a known fashion when the handpiece part is plugged onto the motor cartridge as discussed hereinafter. As illustrated, an annular coupling element 5 having a groove is disposed on the one end of the cartridge and the shaft end 3 extends therethrough. An annular groove of the element 5 coacts with a catch 67 (FIG. 13) of the adapter V or handpiece IV to form a latch device by means of which a handpiece part, which is telescopically received on the outer surface of the cartridge I, is axially retained on the cartridge but is rotatable relative to the cartridge I.

The cartridge I on the other end has a cylindrical heel 6 whose outside diameter is significantly smaller in comparison to that of the cylindrical portion or part 1. The heel 6 as may be seen from FIG. 7 is part of a sleeve 31 which is screwed into the motor cartridge. The sleeve or heel 6 has an axial opening with internal threads 8 for receiving a tappet or pin 7 of a connector part II. The tappet or pin 7 is provided with threads 8a which coact with the threads 8 of the heel 6 to form a non-rotatable rigid but detachable connection between the motor cartridge and the connector part II.

The connector part II is secured on a supply hose 9 which has a plurality of leads or feed lines 10. Two of the feed lines 10 supply air and water to radial discharge openings or ports 11 and 12 on the circumference of the pin 7, which openings 11 and 12 are sealed from one another by O-rings in a conventional manner. Electrical power is supplied on electrical leads and are connected to a pair of axially spaced slide rings 13 on the circumference of the pin and also to contacts 14 disposed at an end of the pin 7. The contacts 14 are composed of a contact socket which is in the center of the pin 7 and of a contact spring situated concentrically thereto. The slip rings 13 serve for supplying electrical energy to an illumination means which will be described hereinafter. The contact pair 14 serve for supplying the necessary electrical energy to the motor 27 of the cartridge I.

A feature of the assembly is a coupling ring III of FIG. 3 which is telescopically received on the heel 6 prior to forming the connection between the pin 7 in the socket of the heel 6. To allow rotation of the coupling member 3 on the heel 6, it is provided with an annular groove which coacts with an annular groove on the heel 6 and receives an O-ring 15. Thus, with the coupling member III assembled on the heel 6, an arrangement such as illustrated in FIG. 7 will be obtained.

After assembly of the coupling member III onto the motor cartridge I and subsequently screwing the connecting pin 7 of the connecting part II to the motor cartridge I, either a handpiece IV of FIG. 4 or an adapter V of FIG. 5 can be alternately attached and latched or secured against axial slipping off of the cartridge I by the above-mentioned latching means. It should be noted that the latching means allows either the handpiece IV or the adapter V to be rotated on the cartridge I. When the adapter V of FIG. 5 is slipped onto the cartridge, then a handpiece VI of FIG. 6 is telescopically mounted on the adapter.

The handpiece IV of FIG. 4 is the type of handpiece part wherein the head housing 17 has chuck means 100 which receives the tool 16 and rotates the tool on the axis thereof. The housing 17 forms a unit with a gripping sleeve 18 which extends up to the motor side and then has an additional tubular sleeve 19 for extending over the motor cartridge I. It should be noted that the sleeve 19 has internal bearing surfaces which are received on the two axially spaced bearing surfaces 2 and 2' of the cartridge. In the plugged-in condition, the motor or drive shaft 3 is coupled by the dog to a drive train 20 which is composed of at least two drive shaft sections that extend through the gripping sleeve 18 to the chuck means 100 so that the movement or rotation of the drive motor shaft 3 will be transferred to rotate the tool 16.

The adapter V (see FIG. 5) contains a sleeve-shaped section 21 and a pilot or guide sleeve 22 extending from one end of the sleeve-shaped section 21. As illustrated, the guide sleeve has a plurality of radial discharge openings 23 axially spaced therealong and separated by O-rings. When the adapter V is secured on the motor cartridge I, the sleeve 22 in addition to surrounding the drive shaft 3 and the dog 4, will receive a socket of a grip piece VI. The socket of the piece VI has corresponding channels which match the radial openings 23 so that fluid such as air and water being transferred through the ports 23 is received and conveyed through the grip piece VI for discharge adjacent the tool 16. In addition, when the grip piece VI is assembled on the adapter V, a drive train 24 of drive shaft sections will be coupled to the dog 4 for transferring rotation of the shaft 3 to drive or rotate the chuck means 100 holding the tool 16. As illustrated, the end of the handpiece VI has a nose 25 which actuates a switch in a manner discussed hereinafter when the handpiece is assembled on the adapter V.

As best illustrated in FIG. 7, the motor cartridge I has an outer housing or cylindrical member 26 that forms the outer surface 1 and receives the rotor 26, the bearings 28, the stator 29 and the bush and bush mountings 30 but does not contain any cooling agent lines or light guides. The heel 6, which carries the coupling member III, is a graduated portion and is connected to a screw-type sleeve 31 which is threaded onto the motor housing 26. The inside diameter of this graduated portion of the sleeve is dimensioned so that the pilot pin 7 of the connection II can be introduced and connected therein to the motor cartridge I via the screw-type connection formed by the threads 8 receiving the threads 8a. When the screw-type sleeve 31 is removed from the housing 26, the brush mounts 30 are accessible, for example, for replacing the carbon brushes. For the purpose of electrical contacts, a cooperating contact pair 32 mate with the contact pair 14 of the pin 7. The contact pair 32 as illustrated include a centrally situated pin and a contact ring which is disposed concentric in an insulated fashion.

The cartridge at the end having the coupling member 5 has channels or openings 33, while channels or openings 34 are provided in the brush mounting 30. These channels 33 and 34, which extend parallel to the axis of the shaft 3, allow cooling air for cooling the motor to circulate through the motor cartridge and as illustrated this air is introduced from the one end as indicated by the arrows to move between the stator 29 and the rotor 27 and subsequently is returned to the supply hose 9 through the brush mount 30. The feed of the cooling air to the inside adjacent the shaft 3 may be seen from FIGS. 11-14 which show the adapter part V.

The coupling member III which is rotatably attached to the heel 6 is a carrier of a light source such as an electrical incandescent lamp 35 which is received in a lamp socket 36 and is turned on by a switch means 37 when either the handpiece part IV or the adapter V with a handpiece VI is assembled onto the motor cartridge I. The coupling member III further contains conduit channels which are required for both the air and the water as well as a flow regulating means for controlling the flow of one or the other agents. As illustrated in FIG. 8, the channels for the air and water terminate in sockets 38 and 39 in a mounting part 40 and are limited to a rather narrow angular region α of about 60° to 70° of the circumference. As illustrated, the lamp and these sockets 38 and 39 are positioned at the end of an end face of the sleeve-like member telescopically received on the motor cartridge I. As illustrated in FIG. 7, the incandescent lamp 35 is situated to extend at an angle relative to the axis of the motor. While this is an advantageous arrangement for space reasons, this arrangement is not absolutely necessary. The lamp can, on the contrary, also be horizontally situated in the mounting part 40, i.e., with the longitudinal axis extending parallel to the motor axis.

As illustrated in FIGS. 8 and 10, the two connecting sockets 38 and 39 for the air and water are situated symmetrically relative to the centrally disposed lamp 35. The agent channels within the coupling member III, for example, the water channel, is best illustrated in FIG. 9. The water is accepted via a channel 42 from an opening 12 in the pin 7 (FIG. 2) and is conducted to an end part 44 containing the socket 38 by means of a flexible hose section 43 which is situated in a hose of the mount part 40. The socket 38 and end part 44 are advantageously replaceably situated in the part 40. The air guide or channel is designed in a separate manner. A control means for determining the flow quantity is additionally provided for the water channel. This control means or valve comprises a ball 45 which is displaced with the assistance of an eccentrically situated cam surface 46 of a set collar 47, which collar 47 can be rotated relative to the member 40 to cause the ball 45 to squeeze the hose 43. The set collar 47 is designed as a two-piece member and composed of a first ring 47a containing the cam surface 46 and a second ring 47b which covers the lamp 35. The part 40 contains axial positioning and dog parts 49 with surfaces 48 to extend parallel to one another and which come into engagement with cooperating surfaces 68 of a cooperating element 69 situated in the handpiece part IV or the adapter V. These cooperating surfaces 48 and 68 form plug means so that when either the adapter V or handpiece IV is coupled onto the motor cartridge I, the coupling member III and the handpiece part or adapter will rotate together on the cartridge I.

The electrical contacting for switching the incandescent lamp 35 on and off is explained in greater detail with reference to FIG. 10. Contact lugs or strips 50 and 51 are resilient and are situated on the part 40. One end of the strip 50 forms part of the lamp socket 36 and the other end which is identified at 52 forms a contact surface for pressing against one of the slip rings 13 of the guide pin 7. The strip 51 has one end which forms part of the socket 36 and has another end 53 which interacts with a spring-loaded trip cam or a switch 37 (FIG. 7). Given an actuation of the trip cam or switch 37, a contact section 56 (FIG. 10) is released so that it will engage a slip ring 13 of the pin 7 to complete the circuit for switching the lamp 35 on. The switch 37 as illustrated in FIG. 7 includes a member 58 which is biased to the position illustrated in FIG. 7 by a spring 54.

The structure of the adapter V will be discussed with regard to FIGS. 11-14. It should be noted that the sleeve-shaped section 21 of the adapter V is telescopically received on the motor cartridge I and provides for the guidance of the agents such as air and water as well as the light has the same structure as the sleeve portion 19 of the handpiece IV of FIG. 4.

The sleeve-shaped section 21 of the adapter V which section extends over the motor cartridge I is composed of a thin outside sleeve 60 forming an outer covering and of an insert part 61 whose inside contour corresponds to the motor cartridge I and, in particular, forms the cooperating internal bearing surfaces which are necessary for rotation and coact with the bearing surfaces 2 and 2'. At its periphery, the insert 61 contains recesses 62 which form an angular space with the outside sleeve 60. In this annular space, pipe lines or conduits 63 and 64, which are for the passage or conducting the air and water and a light waveguide 65 are mounted. In addition, a switch rod 66 is mounted in this annular space. The remaining portions of the annular space can be used for conducting cooling air for cooling the motor. The cooling air first flows through the coupling member III so that the air passes over the lamp 35 to cool it. This air is discharged through the opening such as 57 of FIG. 8 which is on both sides of the lamp 32 and then the air flows into the sleeve 21 at the locations indicated by the arrows in FIGS. 11 and 13. The air flows in the space between the outer sleeve 60 and the part 61 to the end adjacent the guide sleeve 22 where the air will then enter the inside space of the motor through the channel such as 33 when the adapter is placed on the motor cartridge.

The adapter V includes a U-shaped part 69 at the end which is adjacent the coupling member III. The U-shaped part 69 has the parallel surfaces 68 which coact with the surfaces 48 (FIG. 8) of the coupling member III to effect a centering and positioning of the adapter V relative to the coupling member when the adapter is plugged onto the cartridge. This centering and positioning insures that an end 65a (FIG. 12) of the light waveguides 65 are positioned opposite the incandescent lamp 35 and that the ends 63a, 64a of the two agent conduit channels 63 and 64 are engaged into corresponding sockets 38 and 39 of the coupling member III. In the coupled condition, the one end 66a of the switch rod 66 will be lying against a seating surface of the member 58 (FIG. 7) of the switch means 37. As soon as a hand and angle piece of the type shown in FIG. 6 is plugged onto the guide sleeve 22 of the adapter V, the switch nose 25 will press against the other end 66b to shift the switch rod 66 axially so that the end 66a depresses the member 58 against the force of the spring to enable closing the electrical contact for the lamp 35.

As illustrated in FIG. 14, the adapter V adjacent the guide sleeve 22 has an end face which has a circular cross-section lying centrally relative to the motor axis, but at the end that is adjacent the coupling member III as illustrated in FIG. 12, the circular cross-section lies eccentric relative to the motor axis.

Given the employment of a complete handpiece IV such as shown in FIG. 4, the sleeve-shaped part 19 is constructed in a fashion similar to the sleeve 21 of the adapter V. The conduits for the water and air as well as the waveguides for the light are also provided in the sleeve part 19 in the fashion described herein with regard to the adapter and these parts mate with the connecting elements of the coupling member 3.

The handpiece arrangement of the invention is not limited to a drive cartridge which is equipped with an electric motor. On the other hand, it can also be utilized given a drive cartridge having an air motor.

Although various minor modifications may be suggested by those versed in the art, it should be understood that we wish to embody within the scope of the patent granted hereon, all such modifications as reasonably and properly come within the scope of our contribution to the art.

We claim:

1. In a dental handpiece arrangement having a drive motor with a drive shaft, a grip piece having a head housing with chuck means to hold and rotate a tool and a drive train extending in the grip piece to connect the drive shaft to the chuck means, the improvements comprising the drive motor being received in a cylindrical motor cartridge with the drive shaft extending out of a cylindrical coupling element at one end of the cartridge, said coupling element having a smaller diameter than the diameter of the cartridge, said cartridge having a tubular heel of a smaller diameter than the major portion of the cartridge at the other end for releasable connection with a pin member of a supply hose containing electrical leads and water and air lines, said motor cartridge having at least two cylindrical bearing surfaces axially spaced therealong for telescopically receiving internal bearing surfaces of a cylindrical sleeve which may be part of an adapter or part of a grip piece with an integral sleeve, said cylindrical sleeve having a coupling element cooperating with the cylindrical coupling element to form a latch means for securing the sleeve on the motor cartridge and allowing rotation of the sleeve thereon; and a sleeve-shaped coupling member being received on the tubular heel for rotation thereon, said sleeve-shaped coupling member having means forming fluid coupling means for air and water discharging from the pin member and having fluid channels extending from the fluid coupling means to sockets for receiving ends of fluid conduits disposed in the cylindrical sleeve to form a fluid connection therewith so that the fluid is coupled through the coupling member, the sleeve member and into passages of the grip piece for discharge adjacent the chuck means and the coupling member and the sleeve member having coacting parallel extending surfaces to form a plug-like connection between the sleeve member and the coupling member as the sleeve member is telescopically received on the motor cartridge whereby the motor cartridge of the handpiece arrangement provides flexibility to receive both a grip piece which is mounted on a adapter having a cylindrical sleeve and a grip piece with an integral cylindrical sleeve.

2. In a handpiece arrangement according to claim 1, wherein the coupling member has a socket for receiving an incandescent bulb, electrical contacting means for engaging contacts of the pin member of the supply hose, and two sockets for the fluid coupling means being symmetrically arranged relative to the electrical socket.

3. In a handpiece arrangement according to claim 2, wherein each of the fluid conduits and sockets of the coupling means are replaceably disposed in the coupling member.

4. In a handpiece arrangement according to claim 2, wherein the coupling member includes a squeezable hose section forming part of the fluid conduit in a fluid line, a pinch valve member engaging said squeezable hose being actuated by an eccentric cam surface connected to a collar rotatably disposed on the coupling member.

5. In a handpiece arrangement according to claim 4, wherein the rotatable collar is designed in two pieces and contains a first ring portion containing the cam surface and a second ring portion covering the incandescent lamp.

6. In a handpiece arrangement according to claim 2, wherein the electrical contacts for the incandescent light include a switch means comprising a movable member mounted in the coupling member, one of the contact paths for the lamp socket being a resilient member engaging the movable member and adapted to contact a slip ring on the pin member of the supply hose, said resilient member being held out of engagement with the slip ring when the switch member is in one position and being released for engaging the slip ring when the switch member is moved to a second position.

7. In a handpiece arrangement according to claim 1, wherein the coupling member and the tubular heel have coacting grooves receiving an O-ring to form a latch means for holding the parts together and allowing relative rotation therebetween.

8. In a handpiece arrangement according to claim 1, wherein the tubular heel is formed by a reduced portion of a threaded sleeve secured to a housing of the motor cartridge, said threaded sleeve being removable to enable access to motor parts such as brush holders.

9. In a handpiece arrangement according to claim 8, wherein the brush holder contains contacts in the form of an axial contact pin and a ring contact disposed concentrically thereto.

10. In a handpiece arrangement according to claim 1, wherein the motor cartridge has air entry openings at each end, said openings being interconnected by inside space passing through the motor parts.

11. In a dental handpiece according to claim 1, wherein the cylindrical sleeve member is a portion of an adapter having a guide sleeve at one end surrounding the drive shaft of the motor, said handpiece being axially plugged on the guide pin with the drive shaft being coupled to the drive train of the grip piece, said sleeve member having surfaces adjacent the other end engaging corresponding surfaces of the coupling member when the sleeve is plugged onto the motor cartridge to insure alignment of the fluid conduits with the sockets in the coupling member, and alignment of a light waveguide of the sleeve with a light source formed in the coupling member, said fluid conduits extending axially along the sleeve and discharging through radial ports in the guide sleeve and the light waveguide being terminating at an end of the sleeve member adjacent the guide pin.

12. In a dental handpiece according to claim 11, wherein the sleeve member contains a switch rod extending parallel to the axis of the sleeve member, said switch rod having one end engaging a switch provided in the coupling member and the other end being engaged by a nose of a grip piece assembled on the guide sleeve so that assembly of the grip sleeve on the guide sleeve actuates the light source in the coupling member.

13. In a dental handpiece according to claim 11, wherein the sleeve member adjacent the guide pin has a concentric circular cross-section and adjacent the coupling member has a circular cross-section eccentric to the axis of the drive cartridge.

14. In a dental handpiece according to claim 11, wherein the sleeve member is designed as a double wall having a thin outer sleeve and an insert part, said insert part having axially spaced circular bearing surfaces coacting with the bearing surfaces of the motor cartridge when assembled thereon, said insert part and outer sleeve forming an annular space receiving conduits for the fluid, one or more light guides and a switch rod extending between the ends of the sleeve member, the remaining space providing passage for cooling air flowing from the coupling member from the region of an incandescent lamp and being discharged adjacent the guide sleeve for passage back through the motor cartridge, said switch rod being axially displaceable in the sleeve member when a grip piece is assembled on the guide sleeve to apply power to the light source of the coupling member.

15. In a dental handpiece according to claim 1, wherein the sleeve member is a part of the grip piece and is received on the motor cartridge as the grip piece is assembled thereon.

16. In a dental handpiece according to claim 1, wherein the sleeve member is a portion of the grip piece and extends over the motor cartridge when the grip sleeve is connected thereto, said sleeve member having surfaces at its open end coacting with surfaces of the coupling member when the grip piece is assembled on the motor cartridge to form a plug-like connection therebetween, said sleeve member having at least one conduit for a fluid extending parallel to the axis and a light waveguide extending parallel to the axis, said light waveguide receiving light from an incandescent bulb provided in the coupling member.

17. In a dental handpiece according to claim 16, wherein the coupling member contains a spring-loaded actuation element for connecting power to the incandescent bulb, said sleeve member having a switch rod for engaging the actuation element to switch the light on as the grip piece with the sleeve member is assembled on the motor.

18. In a dental handpiece according to claim 16, wherein the sleeve member adjacent the grip piece end has a circular configuration concentric with the drive shaft of the drive cartridge and at an end facing the coupling member has a circular cross-section eccentrically disposed to the drive shaft of the drive cartridge.

19. In a dental handpiece according to claim 16, wherein the sleeve member is designed as a double wall member with a thin outer sleeve and an insert part, said insert part having two axially spaced internal bearing surfaces for engaging the bearing surfaces of the motor cartridge when the grip piece is secured thereon, said thin outer sleeve and insert part forming an annular space for receiving the fluid conduits and light waveguides with the remaining space providing cooling air passing over the incandescent bulb axially along the sleeve to a point adjacent the coupling member of the drive motor cartridge for passage through apertures in the end walls of the motor cartridge for cooling the drive motor.

* * * * *